United States Patent [19]

Rohr et al.

[11] 4,183,743
[45] Jan. 15, 1980

[54] NOVEL HERBICIDALLY ACTIVE, NUCLEAR-SUBSTITUTED PHENOXY-PHENOXY-ALKANECARBOXYLIC ACID DERIVATIVES AND USE THEREOF FOR CONTROLLING GRASS-LIKE WEEDS

[75] Inventors: Otto Rohr, Therwil, Switzerland; Georg Pissiotas, Lörrach, Fed. Rep. of Germany; Beat Böhner, Binningen, Switzerland

[73] Assignee: Ishihara Sangyo Kaisha Ltd., Osaka, Japan

[21] Appl. No.: 926,061

[22] Filed: Jul. 19, 1978

Related U.S. Application Data

[62] Division of Ser. No. 742,311, Nov. 16, 1976, Pat. No. 4,106,925.

[30] Foreign Application Priority Data

Nov. 20, 1975 [CH] Switzerland ............ 15033/75
Nov. 20, 1975 [CH] Switzerland ............ 15034/75

[51] Int. Cl.² ............ A01N 9/12; C07C 153/11
[52] U.S. Cl. ............ 71/100; 260/455 R
[58] Field of Search ............ 71/100, 124; 260/455 R

[56] References Cited

U.S. PATENT DOCUMENTS

| | | | |
|---|---|---|---|
| 2,341,868 | 2/1944 | Hitchcock et al. | 71/115 |
| 2,412,510 | 12/1946 | Jones | 71/118 |
| 2,726,946 | 12/1955 | Mussell | 71/124 |
| 3,333,943 | 8/1967 | Richter et al. | 71/100 |
| 3,420,892 | 1/1969 | Martin et al. | 71/124 |
| 3,953,489 | 4/1976 | Tamura et al. | 71/100 |
| 3,954,442 | 5/1976 | Becker et al. | 71/100 |
| 4,064,269 | 12/1977 | Karrer | 260/455 R |

FOREIGN PATENT DOCUMENTS

49-62632 6/1974 Japan ............ 71/100

Primary Examiner—Glennon H. Hollrah
Attorney, Agent, or Firm—Sughrue, Rothwell, Mion, Zinn and Macpeak

[57] ABSTRACT

The invention is concerned with new herbicidally active 4-phenoxy-α-phenoxy-alkanecarboxylic acid derivatives, especially propionic acid esters of the type

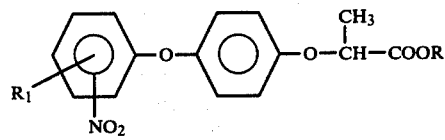

bearing in the first phenoxy radical a nitro group besides another substituent $R_1$ which is preferably a halogen atom, the $CF_3$ group is lower alkyl, alkoxy or alkoxycarbonyl group. The invention is further concerned with herbicidal compositions containing such new derivatives and with methods for the selective control of grass-like weeds in crops of dicotyledonous and monocotyledonous cultivated plants such as cereals.

10 Claims, No Drawings

NOVEL HERBICIDALLY ACTIVE, NUCLEAR-SUBSTITUTED PHENOXY-PHENOXY-ALKANECARBOXYLIC ACID DERIVATIVES AND USE THEREOF FOR CONTROLLING GRASS-LIKE WEEDS

This is a division of application Ser. No. 742,311, filed Nov. 16, 1976, now U.S. Pat. No. 4,106,925.

The present invention provides novel herbicidally active, nuclear-substituted phenoxy-phenoxy-alkanecarboxylic acid derivatives, a process for their manufacture, herbicidal compositions which contain these novel compounds as active ingredients, and a method of selectively controlling grass-like weeds in crops of cultivated plants, which comprises the use of the novel active substances or of compositions which contain them.

The new active compounds have the formula I

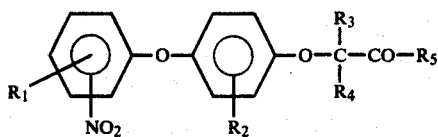

wherein $R_1$ represents a halogen atom, $CF_3$, a lower alkyl, alkoxy or alkylthio group, the cyano group or a $-COR_5$ or

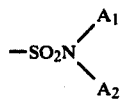

group, wherein each of $A_1$ and $A_2$ represents a hydrogen atom, a lower alkyl or alkoxycarbonyl group, $R_2$ represents a hydrogen atom, a halogen atom or a lower alkyl group, each of $R_3$ and $R_4$ independently represents a hydrogen atom or a lower alkyl group, and $R_5$ represents an OH, $-O-$cation, alkyloxy, alkylthio, alkenyloxy, alkinyloxy, cycloalkyloxy group, an unsubstituted or substituted benzyloxy, phenoxy or phenylthio group, and an $NH_2$, NH-alkyl, $-N(-$dialkyl) or

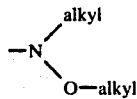

group.

Lower alkyl, alkoxy, alkylthio and alkoxycarbonyl groups represented by $R_1$ and $A_1$, $A_2$ and $R_2$ to $R_4$ are to be understood as meaning herein straight-chain or branched groups containing 1 to 4 carbon atoms. The groups represented by $R_5$ can contain a higher number of carbon atoms and longer alkyl chains (up to 10 carbon atoms), preferably also in this case 1 to 6 or 1 to 4 carbon atoms. Corresponding alkenyloxy and alkinyloxy groups contain up to 4 carbon atoms. Cycloalkoxy groups contain 3 to 12, preferably 5 or 6, carbon atoms. Alkenyloxy groups $R_5$ can contain an additional substituent, such as chlorine.

Possible substituents of phenoxy, phenylthio and benzyloxy groups $R_5$ are one or more selected from the group halogen, alkyl and nitro.

By cations of the $-O-$cation group (represented by $R_5$) are meant mono- and polyvalent cations of inorganic or organic bases, including quaternary ammonium bases, in particular the cations of alkali metal and alkaline earth metal hydroxides. The preferred halogen atom represented by $R_1$ and $R_2$ is chlorine. However, $R_2$ is preferably a hydrogen atom.

Herbicidal compositions containing 4-phenoxy-phenoxy-alkanecarboxylic acid derivatives of similar structure and having a special action on grass for the selective control of grass-like weeds in mono- and dicotyledonous cultivated plants are known from DT-OS No. 2,223,894.

The surprising discovery has now been made that, on account of the presence of a nitro group, the novel active compounds of the formula I of the present invention are clearly superior in their action on grass to the above mentioned active substances of DT-OS No. 2,223,894 as a consequence of their better herbicidal action and/or better selectivity, for example in soya and cotton.

Thus the active compounds of the invention are suitable for the preemergent and especially postemergent selective control of grass-like weeds (for example panic-grasses) of the genera Digitaria, Setaria, Echinochloa, Rottboellia, and also Alopecurus, Apera, Lolium, etc., and especially also *Avena fatua* (wild oats), not only in crops of dicotyledonous cultivated plants (such as cotton, soya, sugar beet etc.), but in particular in crops of monocotyledenous plants as well, such as cereals (wheat, barley, rye, oats), rice etc.

In this respect, and especially for solving the problem of controlling wild oats in wheat, the novel active, compounds and the compositions which contain them constitute a notable enrichment of the stock of technical knowledge.

Some of the active compounds of the invention also possess advantageous growth-regulating effects (growth inhibition).

Particularly preferred active compounds are those of the formula I wherein the substituent $R_1$ represents a halogen atom, in particular a chlorine atom, or $CF_3$. Moreover, it has been observed that a nitro group in the ortho-position and a second substituent in the para-position, such as a chlorine or bromine atom or $CF_3$, imparts a particularly good herbicidal action and selectivity. But compounds with a nitro group in the para-position also have a good action.

Preferred active compounds of the formula I are also those in which $R_2$ is a hydrogen atom, that is to say those which are unsubstituted in the second phenoxy radical.

Compounds in which one of the substituents $R_3$ or $R_4$ is not a hydrogen atom, i.e. which represents for example a lower alkyl group, such as a methyl group, are also important. The simplest ester form ($R_5=OCH_3$) has outstandingly good activity.

The novel compounds of the formula I are obtained by the methods which are known per se for the synthesis of phenoxy-phenoxy-alkanecarboxylic acids and derivatives thereof.

In a first such process, according to the invention a substituted halogeno-nitrobenzene of the formula II.

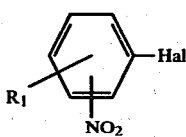

is reacted with a p-hydroxy-phenoxy-alkanoic acid derivative of the formula III

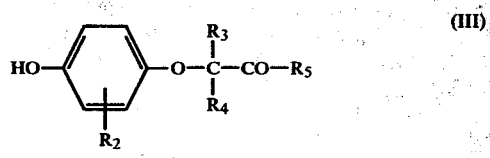

in the presence of a base.

In a second process, according to the invention a start is made from a substituted p-hydroxy-nitrodiphenyl ether of the formula IV

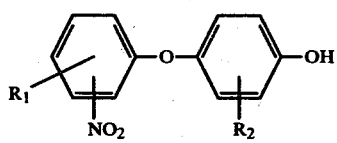

which is then reacted with an α-halogenocarboxylic acid derivative of the formula V

in the presence of a base.

If a carboxylic acid ($R_5=OH$) is used in these processes as starting material of the formulae III and V, then this group can subsequently be converted into another derivative of the formula I as defined herein, for example by esterification etc. Conversely, when using an ester of the formula III or V, the ester group can subsequently be converted into the free carboxylic acid by saponification.

In the formulae II to V of the starting materials, the radicals $R_1$ to $R_5$ are as defined in formula I and Hal represents a halogen atom, such as a chlorine or bromine atom.

The above reactions can be carried out in the presence or absence of solvents or diluents which are inert to the reactants. Polar organic solvents, such as methyl ethyl ketone, dimethyl formamide, dimethyl sulphoxide etc., are preferred. The reaction temperatures are between 0° and 150° C., and the reaction time is from 1 hour to several days, depending on the choice of reaction temperature and solvent. The process is usually carried out at normal pressure. Suitable bases for the reaction are those normally employed, for example KOH, NaOCH$_3$, K$_2$CO$_3$, potassium tert. butylate etc., and also organic bases.

The starting materials of the formulae II to V are partly known. Starting materials of these formulae which have not yet been described can be easily prepared by conventional processes and techniques. Phenoxyphenols of the formula IV can be prepared for example in accordance with the methods described in Journ. Am. Chem. Soc. 61, 2702 (1939) or in Chem. Abstracts 54, 922$^h$ (1960).

The following Examples illustrate the process of the present invention for arbitarily chosen active compounds of the formula I. Further active compounds which are prepared in corresponding manner are listed in the subsequent table.

EXAMPLE 1:

[Methyl 4-(2'-chloro-4'-nitrophenoxy)-α-phenoxypropionate]

6.5 g of pulverised potassium hydroxide and 20 g of methyl 4-hydroxy-α-phenoxypropionate in 250 ml of dry dimethyl sulphoxide are charged at 0° C. into a three-necked flask. With stirring, and at a temperature between 0° and 5° C., 19.5 g of 3,4-dichloro-nitrobenzene are added by small amounts and stirring is continued for 12 hours at room temperature. Thereafter the reaction mixture is poured into ice-water and extracted with ethyl acetate. The extract is dried over sodium sulphate and the solvent distilled off to yield an oily product which is then subjected to high vacuum distillation. The resultant substance, viz. methyl 4-(2'-chloro-4'-nitrophenoxy)-α-phenoxypropionate (yield 27 g), boils at 194° C./0.01 Torr (compound 1).

The methyl-4-hydroxy-α-phenoxypropionate used as starting material is a compound which has not yet been described in the literature and was prepared as follows:

(a) A mixture of 60 g of hydroquinone monobenzyl ether, 50 g of methyl 2-bromopropionate, 42 g of anhydrous potassium carbonate and 500 ml of methyl ethyl ketone, is heated with stirring for 24 hours to reflux temperature. After it has cooled, the reaction mixture is filtered and washed with methyl ethyl ketone. The filtrate is then concentrated in vacuo. The residual oil soon becomes crystalline. Recrystallisation from cyclohexane/petroleum ether yields 82 g of methyl 4-(benzyloxy)-α-phenoxypropionate with a melting point of 67°–68° C.

(b) The stoichiometric amount of hydrogen is introduced at room temperature and normal pressure into a mixture of 57.2 g of methyl 4-(benzyloxy)-α-p-phenoxypropionate, 6 g of palladium charcoal and 600 ml of methanol. When the reaction is complete, the reaction mixture is filtered and the filtrate is concentrated in vacuo. The residual viscous oil is subjected to high vacuum distillation to yield 26 g of methyl 4-hydroxy-α-p-phenoxypropionate with a boiling point of 121° C./0.03 mm.

EXAMPLE 2

(a) Preparation of the starting material methyl 4-hydroxy-α-phenoxypropionate:

A mixture of 60 g of hydroquinone monobenzyl ether, 50 g of methyl 2-bromopropionate, 42 g of anhydrous potassium carbonate and 500 ml of methyl ethyl ketone, is heated with stirring for 24 hours to reflux temperature. After it has cooled, the reaction mixture is filtered and washed with methyl ethyl ketone. The filtrate is then concentrated in vacuo. The residual oil soon becomes crystalline. Recrystallisation from cyclohexane/petroleum ether yields 82 g of methyl 4-(benzyloxy)-α-phenoxypropionate with a melting point of 67°–68° C.

The stoichiometric amount of hydrogen is introduced at room temperature and normal pressure into a mixture of 57.2 g of methyl 4-(benzyloxy)-α-p-phenoxypropionate, 6 g of palladium charcoal and 600 ml of methanol. When the reaction is complete, the reaction mixture is filtered and the filtrate is concentrated in vacuo. The residual viscous oil is subjected to high vacuum distillation to yield 26 g of methyl 4-hydroxy-α-p-phenoxypropionate with a boiling point of 121° C./0.03 mm.

(b) Preparation of an end product therefrom:

4.5 g of pulverised sodium hydroxide and 20 g of methyl 4-hydroxy-α-phenoxypropionate in 300 ml of dimethyl sulphoxide are charged into a sulphonating flask of 750 ml capacity. Then 25 g 4-chloro-3-nitrobenzotrifluoride are added dropwise at room temperature in the course of 10 minutes and stirring is continued overnight at the same temperature. The reaction mixture is poured into ice-water and extracted with methylene chloride. The solvent is distilled off in vacuo to yield a dark oil which is distilled in a high vacuum. Yield: 22 g of methyl 4-(2'-nitro-4'-trifluoromethylphenoxy)-α-phenoxypropionate with a boiling point (0.15) of 176°–179° C. The compounds 1 and 2 prepared in the above Examples, and further active compounds of the formula I, are listed in the following table:

| No. | Position NO$_2$ | R$_1$ | R$_2$ | R$_3$ | R$_4$ | R$_5$ | m.p. °C. | b.p. °C.(Torr) |
|---|---|---|---|---|---|---|---|---|
| 1 | 4 | 2-Cl | H | H | CH$_3$ | —OCH$_3$ | | 194°(0.01) |
| 2 | 2 | 4-CF$_3$ | H | H | CH$_3$ | —OCH$_3$ | | 176°–179°(0.15) |
| 3 | 4 | 2-CF$_3$ | H | H | CH$_3$ | —OCH$_3$ | | 195°(0.5) |
| 4 | 4 | 3-CF$_3$ | H | H | CH$_3$ | —OCH$_3$ | | 194°–205°(0.4) |
| 5 | 2 | 4-Cl | H | H | CH$_3$ | —OCH$_3$ | 71° | 205°(0.01) |
| 6 | 2 | 6-Cl | H | H | CH$_3$ | —OCH$_3$ | 106°–108° | |
| 7 | 2 | 4-COOCH$_3$ | H | H | CH$_3$ | —OCH$_3$ | 91°–92° | |
| 8 | 2 | 4-Cl | H | H | H | —OCH$_3$ | 93°–94° | |
| 9 | 2 | 4-Cl | H | H | CH$_3$ | —OH | 154°–156° | |
| 10 | 2 | 4-Cl | H | H | CH$_3$ | —OC$_3$H$_7$(n) | 43°–45° | |
| 11 | 2 | 4-Cl | H | H | C$_2$H$_5$ | —OC$_2$H$_5$ | 59°–60° | |
| 12 | 2 | 4-Cl | H | H | CH$_3$ | —OC$_3$H$_7$(iso) | 66°–67° | |
| 13 | 4 | 2-CN | H | H | CH$_3$ | —OCH$_3$ | 112°–113° | |
| 14 | 4 | 2-COOCH$_3$ | H | H | CH$_3$ | —OCH$_3$ | 61°–62° | |
| 15 | 2 | 4-Cl | H | H | CH$_3$ | —OC$_4$H$_9$(n) | oil | |
| 16 | 2 | 4-Cl | H | H | CH$_3$ | —OC$_4$H$_9$(iso) | oil | |
| 17 | 2 | 4-Cl | H | H | H | —OC$_4$H$_9$(tert) | oil | |
| 18 | 2 | 4-Cl | H | H | CH$_3$ | —O—CH$_2$—CH=CH$_2$ | oil | |
| 19 | 2 | 4-Cl | H | H | CH$_3$ | —O—CH$_2$—C≡CH | oil | |
| 20 | 2 | 4-Cl | H | H | CH$_3$ | —O-cyclohexyl | oil | |
| 21 | 4 | 2-Cl | H | H | CH$_3$ | —OC$_2$H$_5$ | oil | |
| 22 | 2 | 4-Cl | H | H | CH$_3$ | —OC$_4$H$_9$(sec) | oil | |
| 23 | 2 | 4-Cl | H | H | CH$_3$ | —O-phenyl | oil | |
| 24 | 4 | 3-CN | H | H | CH$_3$ | —OCH$_3$ | 134°–135° | |
| 25 | 2 | 4-Cl | H | H | CH$_3$ | —NH$_2$ | 159° | |
| 26 | 2 | 4-Br | H | H | CH$_3$ | —OCH$_3$ | 67°–68° | |
| 27 | 2 | 4-CH$_3$ | H | H | CH$_3$ | —OCH$_3$ | | 191°(0.04) |
| 28 | 4 | 3-CH$_3$ | H | H | CH$_3$ | —OCH$_3$ | oil | |
| 29 | 2 | 4-Cl | H | H | CH$_3$ | —O—CH$_2$—C(CH$_3$)=CH$_2$ | | 220°(0.02) |
| 30 | 2 | 4-Cl | H | H | CH$_3$ | —O—CH$_2$—CH=C(Cl)—CH$_3$ | 49°–50° | |
| 31 | 2 | 4-Cl | H | H | CH$_3$ | —OCH$_2$—CH=CHCl | oil | |
| 32 | 2 | 4-Br | H | H | CH$_3$ | —OH | 155°–156° | |
| 33 | 4 | 3-COOCH$_3$ | H | H | CH$_3$ | —OCH$_3$ | 81°–82° | |
| 34 | 2 | 4-Cl | H | H | CH$_3$ | —NHCH$_3$ | 122° | |
| 35 | 2 | 4-Cl | H | H | CH$_3$ | —SCH$_3$ | oil | |
| 36 | 2 | 4-CN | H | H | CH$_3$ | —OCH$_3$ | 78°–80° | |
| 37 | 2 | 4-Cl | H | H | CH$_3$ | —NHC$_2$H$_5$ | 111° | |
| 38 | 2 | 4-Cl | H | H | CH$_3$ | —OCH$_2$—C(Cl)=CH$_2$ | oil | |
| 39 | 2 | 4-OCH$_3$ | H | H | CH$_3$ | —OCH$_3$ | oil | |
| 40 | 4 | 3-OCH$_3$ | H | H | CH$_3$ | —OCH$_3$ | oil | |
| 41 | 2 | 4-Cl | H | H | CH$_3$ | 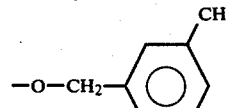 | oil | |
| 42 | 2 | 4-Cl | H | H | CH$_3$ | 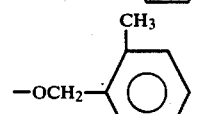 | oil | |

-continued

| No. | Position NO$_2$ | R$_1$ | R$_2$ | R$_3$ | R$_4$ | R$_5$ | Physical Constants m.p. °C. | b.p. °C.(Torr) |
|---|---|---|---|---|---|---|---|---|
| 43 | 2 | 4-Cl | H | H | CH$_3$ | —OCH$_2$—(2,4-dichlorophenyl) | oil | |
| 44 | 2 | 4-Cl | H | H | CH$_3$ | —OCH$_2$—(3,4-dichlorophenyl) | oil | |
| 45 | 2 | 4-Cl | H | H | CH$_3$ | —O—CH$_2$—(2-chlorophenyl) | oil | |
| 46 | 2 | 4-Cl | H | H | CH$_3$ | —O—CH$_2$—(4-chlorophenyl) | oil | |
| 47 | 2 | 4-Cl | H | H | CH$_3$ | —S-phenyl | oil | |
| 48 | 2 | 4-Cl | H | H | CH$_3$ | —N(CH$_3$)(OCH$_3$) | oil | |

The novel active substances of the formula I are stable compounds which are soluble in conventional organic solvents, such as alcohols, ethers, ketones, dimethyl formamide, dimethyl sulphoxide etc.

The compositions of the present invention are obtained in known manner by intimately mixing and grinding active substances of the general formula I with suitable carriers and/or additives, with or without the addition of antifoam agents, wetting agents, dispersants and/or solvents which are inert to the active substances. The active substances may take and be used in the following forms:

solid forms: dusts, tracking agents, granules, coated granules, impregnated granules and homogeneous granules;

active substance concentrates which are dispersible in water: wettable powders, pastes, emulsions, emulsion concentrates;

liquid forms: solutions.

The concentration of active substance in the compositions of this invention is between 1 and 80 percent by weight. As circumstances may require, the active substances can also be applied in low concentrations of about 0.05 to 1 percent by weight.

The compositions of the present invention can be mixed with other biocidal active substances, or compositions. Thus in addition to containing the cited compounds of the formula I, the compositions of the present invention can also contain, for example, insecticides, fungicides, bactericides, fungistatic agents, bacteriostatic agents, nematocides or further herbicides, in order to broaden the activity spectrum.

Granules

The following substances are used to prepare 5% granules:

5 parts of one of the active substances of the formula I,
0.25 parts of epichlorohydrin,
0.25 parts of cetyl polyglycol ether,
3.50 parts of polyethylene glycol,
91 parts of kaolin (particle size 0.3–0.8 mm).

The active substance is mixed with epichlorohydrin and dissolved with 6 parts of acetone, and the polyethylene glycol and cetyl polyglycol ether are then added. The resultant solution is sprayed on kaolin and subsequently evaporated, in vacuo.

Wettable Powder

The following constituents are used to prepare (a) a 70% and (b) a 10% wettable powder:

(a)

70 parts of methyl 4-(2'-nitro-4'-chloro-phenoxy)-α-phenoxypropionate,
5 parts of sodium dibutylnaphthalene sulphate,
3 parts of naphthalenesulphonic acid/phenolsulphonic acid/formaldehyde condensate (3:2:1),
10 parts of kaolin,
12 parts of Champagne chalk;

(b)

10 parts of methyl 4-(2'-nitro-4'-trifluoromethylphenoxy)-α-phenoxypropionate,
3 parts of a mixture of the sodium salts of saturated fatty alcohol sulphates,
5 parts of naphthalenesulphonic acid/formaldehyde condensate.
82 parts of kaolin.

The respective active substance is applied to the corresponding carriers (kaolin and chalk) and then these are mixed and ground, to yield wettable powders of excellent wettability and suspension power. By diluting these wettable powders with water it is possible to obtain suspensions containing 0.1 to 8% of active substances. These suspensions are suitable for controlling weeds in cultivations of plants.

Paste

The following substances are used to prepare a 45% paste:
45 parts of methyl 4-(2'-chloro-4'-nitro-phenoxy)-α-phenoxypropionate or one of the other cited active compounds of the formula I,
5 parts of sodium aluminium silicate,
14 parts of cetyl polyglycol ether with 8 moles of ethylene oxide,
1 part of oleyl polyglycol ether with 5 moles of ethylene oxide,
2 parts of spindle oil,
10 parts of polyethylene glycol,
23 parts of water.

The active substance is intimately mixed with the additives in appropriate devices and ground. A paste is obtained from which, by dilution with water, it is possible to manufacture suspensions of the desired concentration of active substance.

Emulsion Concentrate

The following ingredients are mixed to prepare 25% emulsion concentrate:
25 parts of methyl 4-(2'-nitro-4'-methoxycarbonyl)-phenoxy)-α-phenoxypropionate or one of the other cited active compounds of the formula I,
5 parts of a mixture of nonylphenolpolyoxyethylene and calcium dodecylbenzenesulphonate,
35 parts of 3,3,5-trimethyl-2-cyclohexen-1-one,
35 parts of dimethyl formamide.

This concentrate can be diluted with water to give emulsions in suitable concentrations of e.g. 0.1 to 10%. Such emulsions are suitable for controlling weeds in cultivations of plants.

The novel 4-phenoxy-α-phenoxyalkanecarboxylic acids and their derivatives of the formula I which contain a nitro group in one phenyl nucleus, and the compositions which contain them, possess an excellent selective herbicidal action on grass-like weeds in a wide variety of crops of cultivated plants.

Since the novel active compounds destroy virtually only grass-like weeds and attack broad-leafed (dicotyledonous) plants only to an insignificant extent, they are accordingly suitable for controlling grass-like weeds in crops of all dicotyledonous cultivated plants, such as cotton, soya, sugar beet, leguminosae, celery, clover, lucernes, melons, cucumbers, tobacco etc. In addition, they exhibit a markedly better selectivity, for example in soya, cotton and sugar beet, than do the closely related active substances of DT-OS No. 2,223,894 and of Belgian Pat. No. 831,469 which do not contain a nitro group. A control of maize in soya cultures is also possible.

However, it is particularly surprising that the novel active substances of the formula I also possess an outstanding selectivity in the control of grass-like weeds, especially of Panicum-like weeds, in cultures of monocotyledonous plants, such as cereals (wheat, barley etc.).

Thus panic-grasses of the genera Setaria, Echinochloa, Digitaria, Rottboellia and the like can also be selectively controlled exceptionally well in cultures of monocotyledonous plants, such as wheat and barley etc., in addition to soya.

The novel compounds also have an excellent action against other grass-like weeds, such as Alopecurus, Lolium, Apera, Agrostis etc.

An especially preferred field of use is the selective control of the problem weed *Avena fatua* (wild oats) and its related species in wheat, barley and sugar beet.

Although the novel active compounds of the formula I are effective in pre- and post-emergent application, the post-emergent application in the form of contact herbicides is preferred. But the pre-emergence use is also of interest.

The novel active compounds are preferably formulated for example as 25% wettable powders or for example 25% emulsifiable concentrates and diluted with water, and applied to the plant cultures in the post-emergent stage.

Herbicidal action on applying the active compounds after emergence of the plants (post-emergent application)

Different cultivated plants and grass-like weeds are reared from seeds in pots in a greenhouse until they have reached the 4- to 6-leaf stage. Then the plants are sprayed with aqueous active substance emulsions (obtained from a 20% emulsifiable concentrate) in different rates of application corresponding to 8, 4, 2, 1 and 0.5 kg/hectare. The treated plants are then kept at optimum light, watering, temperature (22°–25° C.) and humidity (50–70% relative humidity) conditions. Evaluation of the test was made 15 days after treatment using the following rating:
9=plants undamaged (as untreated control plants)
1=plants completely withered
8-2=intermediate stages of damage.

Cultivated plants

Triticum (wheat)
Oryza (rice)
Glycine (soya)
Gossypium (cotton)
Beta (sugar beet)

Grass-like Weeds and Undesirable Plants

*Avena fatua*
*Lolium perenne*
*Alopecurus myos.*
*Sorghum hybridum*
*Rottboellia exaltata*
*Digitaria sang.*
*Setaria italica*
*Echinochloa grus galli.*

The result of the test showed that the tested active compounds of the invention of the formula I containing a nitro group exhibit a markedly better selectivity towards wheat, soya, cotton, sugar beet and rice while having a good to better action against grass-like weeds, in that they damage these cultivated plants very much less that the constitutionally closest unsubstituted or chlorinated compounds of DT-OS No. 2,223,894.

We claim:
1. 4-Phenoxy-α-phenoxy-alkanecarboxylic acid derivatives, of the formula:

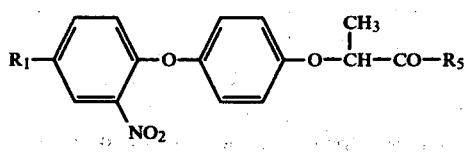

wherein $R_1$ represents a halogen atom; and $R_5$ represents a $C_1-C_4$ alkylthio group, or a phenylthio group.

2. 4-Phenoxy-α-phenoxy-alkanecarboxylic acid derivatives according to claim 1, wherein $R_1$ represents a chlorine atom or bromine atom.

3. Methylthio 4-(2'-nitro-4'-chloro-phenoxy)-α-phenoxypropionate according to claim 1.

4. Phenylthio 4-(2'-nitro-4'-chloro-phenoxy)-α-phenoxypropionate according to claim 1.

5. A herbicidal composition which contains as an active component a herbicidally effective amount of a 4-phenoxy-α-phenoxy-alkanecarboxylic acid derivative of the formula of claim 1, together with a suitable inert carrier therefor.

6. A method for the selective control of grass-like weeds in crops of dicotyledonous and monocotyledonous cultivated plants, which comprises treating the sown cultivated areas before emergence, or the crops of cultivated plants after emergence, with a herbicidal composition which contains as an active component a herbicidally effective amount of a 4-phenoxy-α-phenoxy-alkanecarboxylic acid derivative of the formula (I) of claim 1.

7. A method according to claim 6 which comprises the post-emergent application of the herbicidal composition.

8. A method according to claim 6 for the post-emergent control of *Avena fatua* and Panicum-like weeds in wheat, soya, barley, cotton, or sugar beet.

9. A method according to claim 6, wherein said active component is methylthio 4-(2'-nitro-4'-chloro-phenoxy)-α-phenoxy-propionate.

10. A method according to claim 6, wherein said active component is phenylthio 4-(2'-nitro-4'-chloro-phenoxy)-α-phenoxy-propionate.

* * * * *